(12) United States Patent
Menozzi

(10) Patent No.: US 6,210,006 B1
(45) Date of Patent: Apr. 3, 2001

(54) COLOR DISCRIMINATION VISION TEST

(75) Inventor: Marino Menozzi, Bonstetten (CH)

(73) Assignee: Titmus Optical, Inc., Petersburg, VA (US)

(*) Notice: Subject to any disclaimer, the term of this patent is extended or adjusted under 35 U.S.C. 154(b) by 0 days.

(21) Appl. No.: 09/501,300

(22) Filed: Feb. 9, 2000

(51) Int. Cl.$^7$ ........................................ A61B 3/02
(52) U.S. Cl. ..................................................... 351/242
(58) Field of Search ................................ 351/222, 223, 351/237, 239, 242, 243, 221; 600/558, 310; 345/431

(56) References Cited

U.S. PATENT DOCUMENTS

| | | | |
|---|---|---|---|
| 4,169,285 | * 9/1979 | Walker | 345/431 |
| 4,848,898 | 7/1989 | Massof | 351/242 |
| 5,609,159 | * 3/1997 | Kandel et al. | 351/221 |

OTHER PUBLICATIONS

Measuring Colour Vision Defects, portion of Web Page, www.geocites.com/Hot Springs/8018/Measure.html.
A Rapid Technique To Assess The Resting States Of The Eyes And Other Threshold Phenomena: The Modified Binary Search (MOBS), Tyrrell et al., Psychenomic Society, Inc., vol. 20(2), pp. 137–141, 1988.
36. TeaPP, Abstract–Band, Ludwig–Maximiliams–Universitat, Munchen.
Testing Color Perception with a PC, H. Krueger (with translation).

* cited by examiner

Primary Examiner—George Manuel
(74) Attorney, Agent, or Firm—Millen, White, Zelano & Branigan, P.C.

(57) ABSTRACT

A method for conducting a color discrimination vision test includes displaying a test object comprised of two separate fields wherein one field has a fixed color hue and the other field has a variable color hue. The test subject is instructed to select which field corresponds to a color hue wherein one of the fields is the correct selection. The person makes the selection and the selection is recorded. Subsequent test objects are then displayed that are comprised of the fixed color hue field and the variable color hue field wherein the variable color hue field is a color hue different from the color hue of the previous test object. The display of subsequent test objects is then repeated and the test subject selections are then recorded.

15 Claims, 2 Drawing Sheets

COLOR DISCRIMINATION VISION TEST

BACKGROUND OF THE INVENTION

The present invention relates to a color discrimination vision test and more particularly to an apparatus and method which can be used to identify color vision deficiency and the degree of deficiency, if any, a test subject has.

Color discrimination testing is essential for many types of jobs where the ability of a person to recognize different colors is a fundamental part of a job. Color discrimination testing may also be used for diagnostic purposes to recognize medical conditions that may require attention. Prior art patents, including for instance U.S. Pat. No. 4,848,898 to Massof, describe in detail the human visual system and basic color deficiencies that may be discovered.

Several different tests are widely recognized and practiced. These tests include Ishihara plates, the Munsell-Farnsworth test, and Nagel's anomaloscope.

Ishihara's plates require the detection of numbers which are displayed in front of a background. The numbers and background are built up by spots varying in diameter and in hue. The hue of the spots is selected such as to cause confusion in color perception in color deficient people. Therefore, color deficient people are not able to group those spots together to form the number which is to be detected. Ishihara plates are used to detect red-green color deficiency. A short version of the test is used to determine color vision performance in a passed/failed manner for red or green color vision. The full test can additionally discriminate between "strong" and "weak" deficiency in color vision (two levels). Ishihara's test is very popular in clinical use as well as in the laboratory. Since the colors on the plate are produced by reflection of ambient light, the ambient light must have a specific spectrum (daylight) and must be of a give luminance (>500 lux) to ensure correct test conditions.

In the Farnsworth-Munsell test, 15, 65 or 100 filled circles (depending on the test) of varying hue are placed in random order on a table. The patient is asked to order the circles in a row so that neighboring circles differ as least as possible in color. The first color (hue=blue) in this row is fixed and given by the test. The Farnsworth-Munsell color test requires similar conditions for illumination as mentioned above for the Ishihara test. The interpretation of the results is somewhat more complicated than is the case for the Ishihara test. However, Farnsworth-Munsell enables an administrator to check for red-green as well as for blue yellow deficiency. Detection of degree of deficiency depends on one hand on the number of color circles used. An increasing number of circles goes in parallel with an increasing time needed to complete the test. For this reason, most administrators prefer to use the Farnsworth-Munsell version with 15 circles. On the other hand, the degree of deficiency can also be assessed (two levels) by using a desaturated version of the Farnsworth-Munsell test. However, this procedure sometimes makes the interpretation of results somewhat complicated (e.g. in the case where patients perform better in the desaturated test than in the standard test).

In the so called anomaloscopes (e.g. the Nagel anomaloscope), patients match the hue of two fields. One of the fields has a given hue. The complete anomaloscope test should be performed for different levels of luminance of the field with a fixed hue. The matching procedure consists in varying the luminance of two colors (in case of the red-green test, red and green) which are mixed and comparing the hue of the mixture to the hue of the field with a fixed hue.

Ishihara's test requires the test subjects to communicate the number detected. If the numbers are communicated verbally, the presence of a person is required to record the response. Recording of the information without a test administrator would require test subjects, e.g., to key in the number on a keyboard or a key pad. They therefore would have to change their fixation from the test plates to the keyboard. Beside ergonomical problems, the change of fixation will alter the state of a patient's visual system (e.g. change in level of adaptation) affecting therefore, the result of the test. Similar conditions are also true for the Farnsworth-Munsell and anomaloscope tests mentioned above.

SUMMARY OF THE INVENTION

Accordingly, it is an object of the present invention to overcome the foregoing drawbacks and provide a color discrimination vision test method and apparatus that can be used to identify color vision deficiency and the degree of that deficiency, if any, of a test subject.

In one embodiment, the invention is a method of conducting a color discrimination vision test for a person. The method comprises several steps including displaying a test object comprised of two separate fields wherein one field has a fixed color hue and the other field has a variable color hue. The person being tested is then instructed to select which field corresponds to a color hue wherein one of the fields is the correct selection. The person's selection is recorded. Then, subsequent test objects are displayed that comprise the fixed color hue field and the variable color hue field wherein the variable color hue field is a color hue different from the color hue of the previous test object. The instructing and recording steps are then repeated. In a further embodiment, the color hue of the variable color hue field in the subsequent test objects is preselected to facilitate determination of how well a person discriminates between the fixed color hue and the variable color hue. Also, the fixed color hue can be yellow and the variable color hue can be green or red. Additionally, the variable color hue fields in the subsequent test objects are determined using a modified binary search technique. The subsequent test objects are displayed until there is a predetermined number of incorrect responses recorded or until there is a predetermined minimal difference in the color hues of the two fields. Preferably, the test is self administered without the need of an administrator being present.

In another embodiment, the invention is an apparatus for conducting a color discrimination vision test for a test subject. The apparatus comprises an image display adapted to display a plurality of test objects comprised of two separate fields wherein one field has a fixed color hue and the other field has a variable color hue. The apparatus includes a test subject input device and means for recording input from the test subject input device. The apparatus also includes means for controlling test objects displayed on the image display wherein the variable color hue field changes with the plurality of test objects displayed. In other embodiments, the test subject input device is adapted to be used blindly by a test subject. The test subject input device may also be a joystick.

DETAILED DESCRIPTION OF A PREFERRED EMBODIMENT

Figure 1:
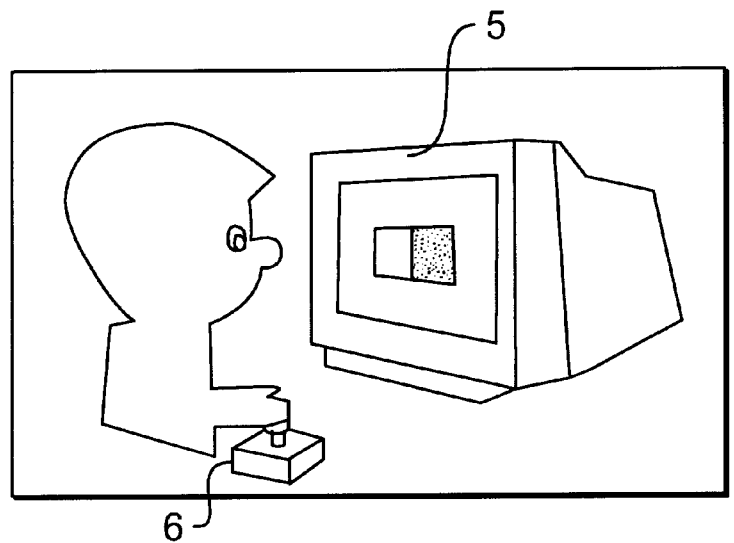
FIG. 1 is a perspective view of an image display showing sample test objects.

FIG. 1 illustrates an image display 5. The image display 5 is used to display test objects that will be used in the color vision test. The image display 5 may be any type of screen or monitor. The only requirement is that the screen have variability in the hues of colors that it can display. The image display 5 can be a simple computer monitor without any privacy or security viewing features. Alternatively, the image display may be incorporated into a vision screening device whereby the image display is only visible to a test subject who is having their color vision analyzed. In view of the foregoing, the image display can be a conventional monitor, an LCD screen, a screen onto which slides may be projected, or any other type of screen on which images can be displayed. Preferably, the image display is incorporated into a vision screening device that offers some level of security so that the test subject can be the only person viewing the particular image display. This cuts down on the opportunity for cheating or other inaccurate results caused by, for instance, glare.

Figure 2:
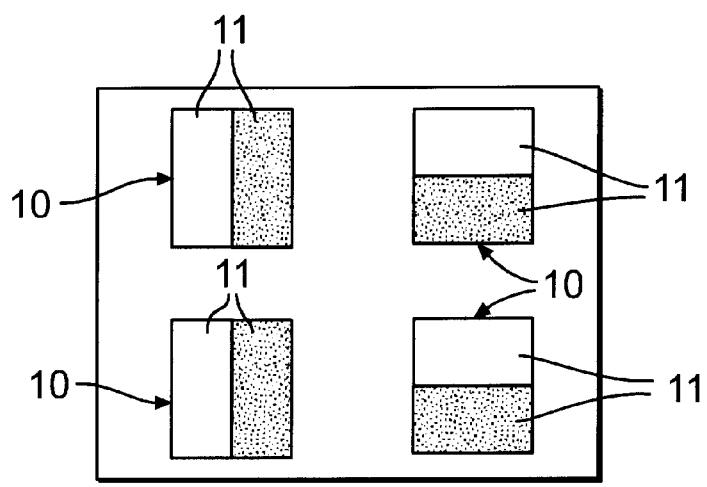
FIG. 2 is an illustration of one preferred embodiment demonstrating four possible orientations of the rectangles of the test field for color testing.

FIG. 2 illustrates four different orientations of test fields 11 that can be used as a test object 10 for color testing. The actual test image merely displays one pair of the test fields 11. The different orientations of the rectangles of the test fields 11 are simply used to ensure the randomness of the testing to obtain accurate results. During the test, one of the fields 11 will always be a fixed color. The color of the second field 11, the variable color hue field, will vary based on the test subject's decisions made during the test. The fixed color hue field is placed adjacent to but aligned with the variable color hue field. The actual orientation of the test fields and the test object is determined by random selection. While adjacent rectangles have been found to be effective, the shapes of the test fields may be different, i.e., two circles, two squares, one circle and one square, etc.

In order to implement the test, a test subject input device is used. Preferably, the apparatus is equipped with only one input device, and it should be able to be used blindly. In a preferred embodiment, a joystick 6 is used to indicate the position (up, left, down, right) of the field of a specific color. This joystick 6 can be used blindly. Other types of input devices can be used to allow the vision test to go forward blindly, thereby not requiring the presence of a person to administer the test and not requiring a test subject to alter their gaze to answer a questions.

Execution of the color test is based on a bracketing technique by which the threshold for color discrimination is assessed. The threshold for color discrimination is defined by difference in hue of fields needed to discriminate the fields from each other. Pairs of fields are displayed to a test subject. One of the two fields is a fixed color hue. The second field will vary. For instance, a test subject is asked to indicate the position of the field of a given color (e.g. red, green, blue, or yellow). There is only one correct selection. The test subject must make a choice by force using the joystick. The test subject's answer determines the amount and direction of change in color to be applied to the color of the field with the variable color hue. The variation is such as either to make the color hue of the field with varying color to become more similar to the color of the field with the fixed color, or it is such as to make the varying color field become more different from the color of the field with the fixed color. The test proceeds until a given set of stopping criterion is reached. The preferable stopping criterion are a given number of incorrect answers or a given minimal difference in the color of the two fields of the test image that can be distinguished by the test subject.

The color test apparatus also includes a means for recording the input from the test subject input device as well as a means for controlling the test objects that are displayed on the image display. Personal computers, LANs or any other networks may be used to control the test objects displayed. The specific protocol of a given apparatus will vary depending on the ability of the image display to display different color hues. Also, the specific protocol of the test may vary depending on the use of the test results. In other words, some test may be more sensitive than others. Some tests may simply be a qualitative pass-fail test. Other tests may attempt to quantitatively evaluate specific color deficiencies. Scientists and computer programmers will know how to specifically implement a test that is desired or required for a particular application. The results are preferably stored, typically in the same CPU that controls the test object display, so that they can be reported or compared to, for instance, contemporaneous tests of others or past tests of a particular test subject sample group. Again, a particular scientist or administrator can create the particular parameters of a desired test.

The invention will be described now in connection with a specific red-green color deficiency test. In this test, the fixed color hue field is a shade of yellow. For potential comparability of this test with other test methods available, the "yellow" hue used in the test is the same or similar to the "yellow" used in Nagel's anomaloscope. This is a specific yellow produced by monochromatic yellow with a wave length l=589.3 nm. The color test is conducted for each combination of color (e.g. red-yellow and green-yellow). The color test is preferably repeated twice for each combination of color to make sure that the test results are accurate. The first match carried out starts out from the most "red" hue. The starting red color is l=650 nm. Using the bracketing technique, a plurality of tests objects is displayed to a test subject. In each case, the test subject identifies the most "red" hue. As noted earlier, this test is conducted until there is a predetermined number of incorrect answers or a predetermined minimal difference in color of the two test fields. The test is then conducted using a green-yellow combination wherein the variable color hue field starts with a green hue. This green has a wave length l=505 nm. Once this second analysis is completed, the two thresholds of color discrimination are assessed. The two thresholds can be considered as boundaries defining the color range within which discrimination of the two colors is concluded. The width of this range is used to characterize the ability of discriminating the two colors.

Any types of testing techniques may be used to arrive at the thresholds of color discrimination. Preferably, a bracketing technique is used for its efficiency and accuracy. Even more preferably, a modified binary search technique is used. This technique, also referred to as the MOBS technique, is described in Tyrrell, R. A., Owens, D. A., *A Rapid Technique To Access The Resting States Of The Eyes And Other Threshold Phenomena: A Modified Binary Search (MOBS), Behavioral Research Methods Instruments & Computers*, 1988, 20(2), 137–141. In general terms, the MOBS technique applied to the color test includes starting by presenting a test image with the variable color hue half way between the boundaries of the test range. The boundaries of the test range in the example discussed earlier are the yellow—589.3 nm (or any other fixed color hue) and red—650 nm (or any other variable color hue being analyzed). Depending on the test subject's answer (correct or incorrect), intensity of feature (color, contrast or whatever else is tested) is increased or decreased by half the amount of difference of intensity given by the values of the boundaries. After two consecutive answers with the same sign (correct or incorrect) have been recorded, the color hue of the test object is set to a value corresponding to the opposite of the range of actual testing (i.e., outside the actual test range), to test for consistency of answer (will the test subject really give an opposite answer?). If the test in the opposite range fails, boundaries are reset to previous values and the test continues. If the test result is okay, the boundaries are changed to reduce the test range and the test proceeds with the narrowing bracketing technique.

Figure 3:
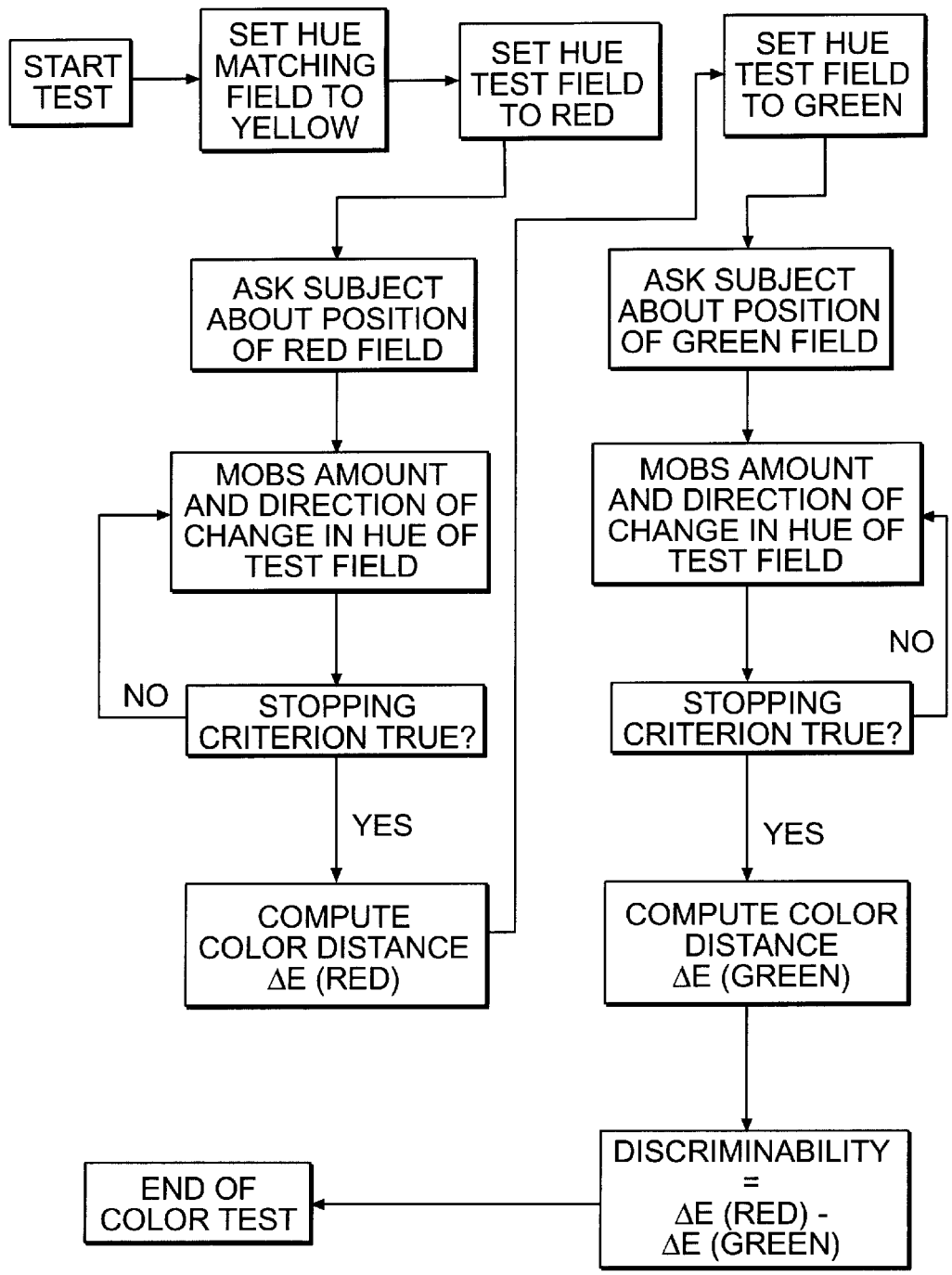
FIG. 3 is a flow chart of an example of a color test for testing red-green vision deficiency.

FIG. 3 is an illustrative flow chart for testing red-green deficiency as described above. The fixed color hue field is the yellow described earlier. The first variable test field is red. And then the second variable test field is green. The test result value ΔE represents the distance in color coordinates between the threshold between for discrimination of yellow/red and yellow/green.

The illustrated example is a test for red-green deficiency. This test may also be adapted for blue-yellow deficiency or any other types of color deficiencies that may be identified and/or developed. In these tests, the fixed color hue field will need to be adjusted to allow the comparison of the variable color hue fields to the fixed color hue field. In any event, the same fundamental procedures will apply.

The interpretation of the results of this test can only be hypothesized. The threshold of color discrimination will preferably be expressed in terms of color coordinates. The C.I.E. 1976 u'v' color coordinates. The difference between the color coordinates of the various color thresholds can be taken as a measure of the ability of the person being tested to discriminate color. In other words, large differences between the color coordinates means a high degree of color deficiency. The exact interpretation of the value will be developed as data is collected based on use of this test. The information that can be gathered will include the following:

a) the percentile of population to which the test subject belongs and/or b) classification of test subject in terms of a pass-fail criterion. Many other different uses and/or conclusions may be developed during the testing.

Thus, what has been described is a color vision test capable of producing accurate test results in connection with a wide variety of test subjects. While the invention has been described in connection with what is presently considered to be the most practical and preferred embodiments, it is to be understood that the invention is not limited to the disclosed embodiment, but, on the contrary, is intended to cover various modifications and equivalent arrangements included within the spirit and scope of the appended claims, which scope is to be accorded the broadest interpretation so as to encompass all such modifications and equivalent structures.

What is claimed is:

1. A method of conducting a color discrimination vision test for a person, the test comprising the following steps:

(a) displaying a test object comprised of two separate fields wherein one field has a fixed color hue and the other field has a variable color hue;

(b) instructing the person being tested to select which field corresponds to a color hue wherein one of the fields is the correct selection;

(c) recording the person's selection; and (d) displaying subsequent test objects comprised of the fixed color hue field and the variable color hue field wherein the variable color hue field is a color hue different from the color hue of the previous test object and repeating the instructing and recording steps.

2. The method of claim 1, further wherein the color hue of the variable color hue field in the subsequent test objects is preselected to facilitate determination of how well a person discriminates between the fixed color hue and the variable color hue.

3. The method of claim 2, wherein the fixed color hue is yellow and the variable color hue is green.

4. The method of claim 3, further comprising repeating steps (a) through (d) wherein the fixed color hue is yellow and the variable color hue is red.

5. The method of claim 2, wherein the fixed color hue is yellow and the variable color hue is red.

6. The method of claim 4, further comprising repeating steps (a) through (d) wherein the fixed color hue is yellow and the variable color hue is green.

7. The method of claim 2, wherein the variable color hue fields in the subsequent test objects are determined using a modified binary search technique.

8. The method of claim 1, wherein the subsequent test objects are displayed until there is a predetermined number of incorrect responses recorded.

9. The method of claim 1, wherein the subsequent test objects are displayed until there is a predetermined minimal difference in the color hues of the two fields.

10. The method of claim 1, further wherein the test is self-administer ed without the need of a human administrator being present.

11. An apparatus for conducting a color discrimination vision test for a test subject comprising:

(a) an image display adapted to display a plurality of test objects comprised of two separate fields wherein one field has a fixed color hue and the other field has a variable color hue;

(b) a test subject input device;

(c) means for controlling test objects displayed on the image display wherein the variable color hue field changes with the plurality of test objects displayed; and (d) means for recording input from the test subject input device.

12. The apparatus described in claim 11, wherein the test subject input device is adapted to be used blindly by the test subject.

13. The apparatus described in claim 12, wherein the test subject input device is a joystick.

14. The apparatus described in claim 11, wherein the means for controlling test objects displayed employs a modified binary search technique.

15. The apparatus described in claim 11, wherein the test is self-administered without the need of a human administrator being present.

* * * * *